United States Patent
Graves et al.

(10) Patent No.: US 6,597,965 B2
(45) Date of Patent: Jul. 22, 2003

(54) METHOD FOR MAKING A PROSTHETIC COMPONENT COSMETIC COVER

(75) Inventors: Ronnie N Graves, Webster, FL (US); Jeffrey J. Peterman, Lubbock, TX (US)

(73) Assignee: Prosthetics Research Specialists, Inc., Bushnell, FL (US)

( * ) Notice: Subject to any disclaimer, the term of this patent is extended or adjusted under 35 U.S.C. 154(b) by 251 days.

(21) Appl. No.: 09/853,297

(22) Filed: May 11, 2001

(65) Prior Publication Data

US 2002/0169515 A1 Nov. 14, 2002

(51) Int. Cl.[7] .............................................. G06F 19/00
(52) U.S. Cl. ...................... 700/159; 700/182; 623/27; 623/901
(58) Field of Search ................................. 700/117, 118, 700/159, 160, 180–186; 623/27, 901; 606/88; 409/64

(56) References Cited

U.S. PATENT DOCUMENTS

| | | | |
|---|---|---|---|
| 4,735,754 A | 4/1988 | Buckner | 264/40.1 |
| 5,152,800 A | 10/1992 | Rothschild et al. | 623/33 |
| 5,336,270 A | 8/1994 | Lloyd | 623/33 |
| 5,539,649 A | 7/1996 | Walsh et al. | 364/474.05 |
| 5,781,652 A | 7/1998 | Pratt | 382/128 |
| 5,824,111 A | 10/1998 | Schall et al. | 623/33 |
| 5,880,964 A | 3/1999 | Schall et al. | 364/474.01 |
| 5,888,216 A | 3/1999 | Haberman | 623/36 |
| 5,901,060 A | 5/1999 | Schall et al. | 364/468.04 |
| 5,980,803 A | 11/1999 | Slemker et al. | 264/222 |
| 5,993,487 A | 11/1999 | Skardoutos et al. | 623/38 |
| 6,083,265 A | 7/2000 | Shorter et al. | 623/27 |

Primary Examiner—Jayprakash N. Gandhi
(74) Attorney, Agent, or Firm—Pettis & Van Royen, P.A.

(57) ABSTRACT

A method for fabricating a foam cosmetic cover for a prosthetic component. The steps comprise selection of an appropriate prosthetic component, collecting data regarding its shape from a replica of the prosthetic component, converting the data into the dimensions of two halves of an interior cavity, and providing this data to a computer-controlled milling machine. The computer-controlled milling machine then cuts a portion of one-half of the cavity into one side of the block and a portion of the other half of the cavity on the opposed side of the block. The cutting head is then advanced longitudinally so that additional portions of the cavity can be cut into the opposing sides of the block. The block is then removed from the milling machine and cut in half longitudinally between the indentations in the sides of a block. The two halves of the block are then attached to one another to form a cavity having the general shape of the prosthetic component.

6 Claims, 9 Drawing Sheets

METHOD FOR MAKING A PROSTHETIC COMPONENT COSMETIC COVER

BACKGROUND OF THE INVENTION

1. Field of the Invention

The present invention relates to a method for fabricating a cosmetic cover for a prosthetic component, particularly cosmetic covers constructed from foam material.

2. Description of the Prior Art

Annually there are a large number of amputations, each resulting in the need for a prosthesis to replace the missing limb. The individual prosthetic components have few aesthetic qualities. For example, the prosthetic components of a prosthetic leg are designed to provide structure that is capable of supporting the body and to provide structure that is capable of mechanical movement as close to human movement as possible. Such structure may include metal tubes, mechanical joints, etc.

It is well known that resilient elastomeric materials may be formed around the mechanical parts of the prosthesis, for example the ankle and foot portion, while shaped foam sleeves may be mounted over the longer tubular portions of the prosthetic components to simulate a leg that matches the sound one. The inner surface of the foam sleeve closely fits around the prosthetic component, while the outer surface is shaped to correspond generally to the shape of the human limb.

The preparation of a foam sleeve for use as a cosmetic cover has long been a manual task. A prosthetic component is selected that is appropriate for the needs of the individual's physical attributes. The interior cavity of the foam sleeve is carved by hand to receive the prosthetic component therein. Hand carving is a tedious and labor intensive task, with the sleeve frequently being loose and ill fitting. Once the interior has been carved the exterior of the sleeve may be carved and smoothed to the desired shape.

The patent issued to Schall et al., U.S. Pat. No. 5,880,964 discloses an automated method for fabricating a cosmetic cover for a prosthetic limb. Using this method the technician takes measurements of the prosthetic components and the socket with a digitizing tool after the prosthetic components and socket have been fitted to an individual. These measurements are forwarded to a CAD system that calculates the interior dimensions from the exterior dimensions previously measured. The dimensions are downloaded to a milling machine, and the milling machine separately carves two mating longitudinal halves of the cosmetic cover from two separate cover blanks. The two separate halves are then attached to one another to form the sleeve.

Hand carving is a manually intensive task which relies upon a considerable amount of trial and error to achieve a properly fitting sleeve. The Schall '964 patent discloses an automated method that includes taking measurements directly from a prosthesis; however, measurements taken by a digitizing tool directly from the metallic prosthetic components are generally inaccurate and require considerable adjustment. Also, mounting a "carving blank" in a milling machine in the normal manner results in cuts that are uneven and that are of poor quality.

It is clear that there is a need for a method of cutting the interior cavity and the exterior surface of a cosmetic cover that is fast and accurate.

SUMMARY OF THE INVENTION

The present invention relates to a method for fabricating a cosmetic cover for a prosthetic component, particularly cosmetic covers constructed from foam material. Most simply stated the steps of this method comprise the selection of a prosthetic component appropriate for the patient, collecting data regarding its shape, providing this data to a computer-controlled milling machine, and cutting a cavity in the foam blank to the proper shape and size.

Prosthetic components may be of many different shapes and sizes depending upon the particular use intended; that is, what portion of a patient's limb will the component replace. For example, the patient may require a below the knee, above the knee, below the elbow or above the elbow prosthesis. Additionally, there are many different manufacturers of such components and each component has a different shape. To provide a tight fit, the exterior dimensions of the prosthetic component must be carefully measured and provided to a computer having Computer Aided Design (CAD) capability. The computer is programmed to manipulate the data into the format required by a computer-controlled milling machine. The exterior dimensions must be converted into the dimensions of an interior cavity sized to receive the prosthetic component. Those dimensions are then separated longitudinally into two parts to provide two longitudinal halves of that cavity. This data is then downloaded into a computer-controlled milling machine for cutting the cavity in a foam block.

The milling machine has a pair of longitudinally opposed rotatable shafts lying along the milling machine's axis of rotation, and a foam block is mounted therebetween for rotation. The milling machine has a cutting head designed for movement toward and away from the axis of rotation and longitudinally parallel to the axis of rotation. The cutting head is controlled by a computer having the proper dimensions stored therein, so that the cutter, mounted in the cutting head, engages one side of the block cutting a portion of one-half of the interior cavity therein as the block rotates. As the block continues to rotate, the cutter engages the opposed side of the block to cut a portion of the other half of the interior cavity therein, creating indentations in both opposed sides of the block. The cutter is then advanced longitudinally along the block so that it may cut portions of the cavity with each rotation until the total cavity is cut in the opposed sides of the block. The block is then removed from the milling machine and cut in half longitudinally between the indentations. The two halves of the block are then attached to one another so that the perimeters of the indentations coincide and a cavity having the general shape of the prosthetic component is formed.

The invention accordingly comprises an article of manufacturer possessing the features, properties, and the relation to elements which will be exemplified in the article hereinafter described, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which.

Similar reference characters refer to similar parts throughout the several views of the drawings.

DESCRIPTION OF A PREFERRED EMBODIMENT

A prosthesis is generally considered to be the total structure commonly used to replace a missing limb, including prosthetic components, a socket and a cosmetic cover. Various prosthetic components are available to provide the structure necessary to form an equivalent of the limb being replaced. Such components include: metal tubes, mechanical joints (for example a mechanical knee joint), shock absorbing structures, etc. all the structure that permits movement as close to natural movement as possible. The prosthesis socket, not shown, provides the connection between the prosthetic components and the residual limb. A cosmetic cover is applied to the prosthetic components and possibly to the socket to provide a more aesthetic appearance to the prosthesis. This invention comprises a method for fabricating a cosmetic cover for the prosthetic components of a prosthesis.

This method may be used for constructing cosmetic covers for arm or leg prosthetic components; however, for illustrative purposes only, this discussion will primarily discuss the method of making a cosmetic cover for components of an above the knee prosthesis, those components that extend from the knee joint to the ankle joint. Separate prosthetic covers will be constructed to cover from the knee joint to the socket and the ankle and foot. There are many available prosthetic components, each having a different shape and size. The method disclosed and claimed herein can be used for any of these prosthetic components. And as previously mentioned, this method for making a cosmetic cover can also be used to cover the prosthetic components for an arm prosthesis or a below the knee prosthesis.

Figures 1, 2A:
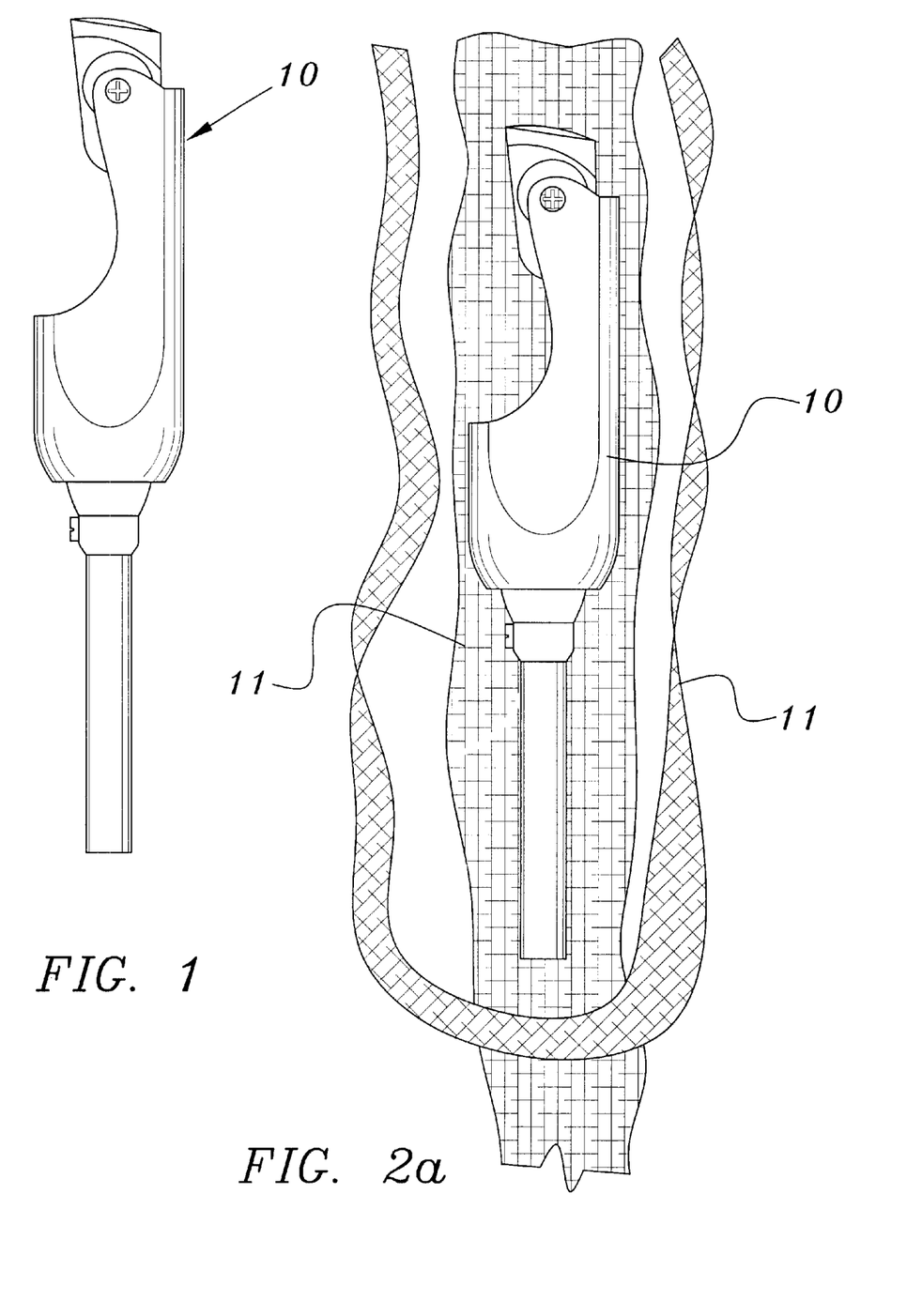
FIG. 1 A left side elevational view of a prosthetic component.
FIG. 2a a left side elevational view of a prosthetic component, illustrating wrapping the prosthetic component with plaster cloth to create a mold thereof.

FIG. 1 discloses one example of a prosthetic component, identified as 10, which is used for illustrative purposes. The first step in constructing a cosmetic cover for this or any prosthetic component, comprises taking accurate measurements of the exterior surface of the prosthetic component. Such measurements can be taken manually using various measuring tools including rulers, calipers, etc. However, measuring the exterior surface of the prosthetic component using digitizing equipment tied to a CAD system is more accurate and much quicker than any manual method. One problem with digitizing equipment is that it is unable to accurately take measurements from metallic materials. As most prosthetic components are made from metal, digitizing equipment used to directly measure prosthetic components is inadequate.

Figure 2B:
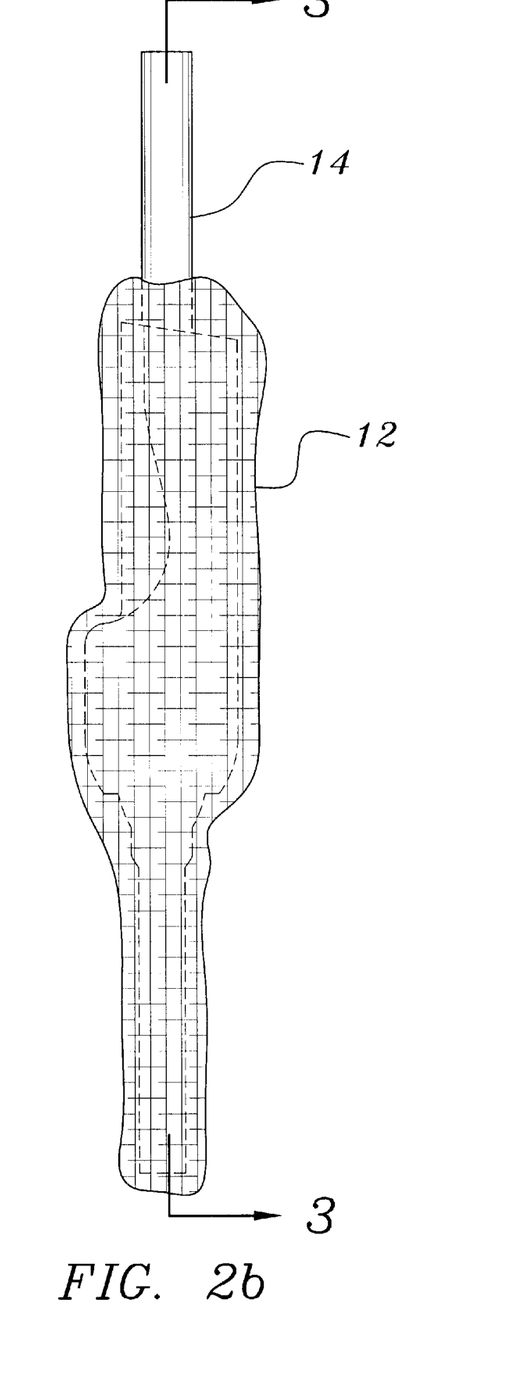
FIG. 2b a left side elevational view of the mold of the prosthetic component.
Figure 3:
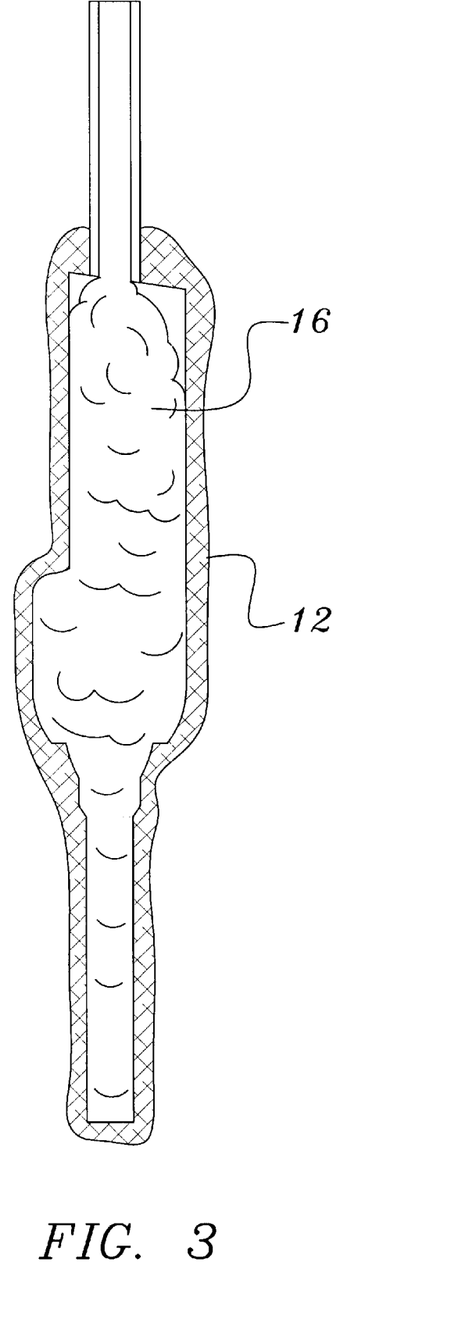
FIG. 3 a left side elevational view of the mold of the prosthetic component illustrating the mold being filled with material capable of setting in a hardened form creating a replica of the prosthetic component.

The first step in the measurement process is to make a mold of the prosthetic component 10. There are many different ways of making a mold, one of the simplest is to wrap the prosthetic component 10 with damp plaster impregnated cloth 11, as shown in FIG. 2a, similar to the cloth used to make plaster casts to hold broken bones in proper alignment while healing. FIG. 2b illustrates a mold 12 with the component 10 removed and the mold 12 resealed leaving a fill pipe 14 projecting from the mold. FIG. 3 is a cross-section of FIG. 2b that illustrates the mold being filled with plaster 16, which then hardens to form a replica 18. The mold 12 is then stripped from the plaster replica 18 and the replica is clamped in a fixed position so that measurements may be taken.

Figure 4:
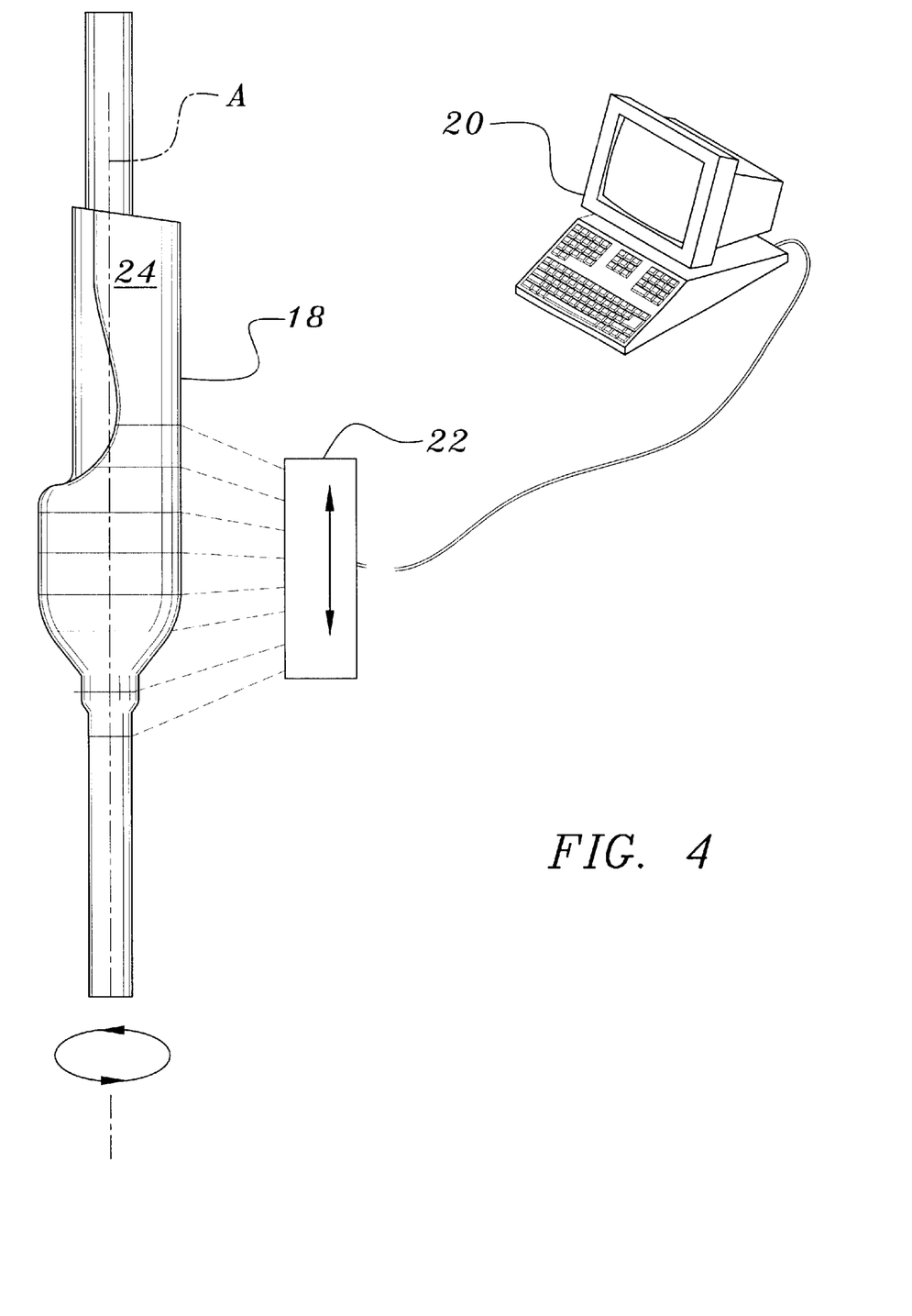
FIG. 4 a V side elevational view of the replica of the component, illustrating taking exterior measurements of the replica using typical digitizing equipment.

As shown in FIG. 4, a computer-aided design (CAD) system 20 with a digitizing wand 22 is used to take the exterior measurements of the replica 18. Any number of CAD systems and digitizing wands will be suitable for the purpose, for example, a Tracer CAD, Premier unit (as described in U.S. Pat. No. 5,781,652) sold by Tracer Corporation of Florida and a mechanical digitizer or a three dimensional lazer digitzer will work very satisfactorily. The wand 22 is passed over the exterior surface 24 of the replica 18 in accordance with the procedures provided by the manufacturer of the digitizer. Once an accurate image has been displayed on the CAD system monitor, the measurements are stored therein. The plaster replica 18 may be used to assist in the shaping of the exterior surface of the cosmetic cover, which will be explained below. For a one time use, the plaster replica 18 will be quite satisfactory; however, since this particular prosthetic component may be required for many additional prostheses, these measurements are downloaded to the computer controlled milling machine so that a foam replica 26 may be cut from a foam block to those exterior dimensions loaded in the CAD system. The outer surface 27 of the replica 26 is then covered with a textile or graphite composite material saturated with a liquid resin to provide a hard but yet flexible exterior surface that will retain its shape during repeated use.

A software program, readily available to those skilled in the art, is loaded into the CAD system to convert the exterior dimensions of the plaster replica 18 into the interior dimensions of a cavity, and the dimensions of the cavity are longitudinally split along the longitudinal axis of rotation A of the replica 18 forming two halves of the cavity. The dimensions of these two separate halves of the cavity, a first half and a second half, are downloaded to the computer controlled milling machine. The computer controlled milling machine is programmed to cut a first half in one side of a foam block 60 and the second half in the opposing side 62 of the foam block 56. These utility programs for converting the exterior dimensions into the dimensions of an interior cavity, for splitting that cavity into two longitudinal halves and for cutting the shapes of those halves into a foam block are simple programs, well within the capability of those skilled in the art and will not be discussed further.

Figure 5:
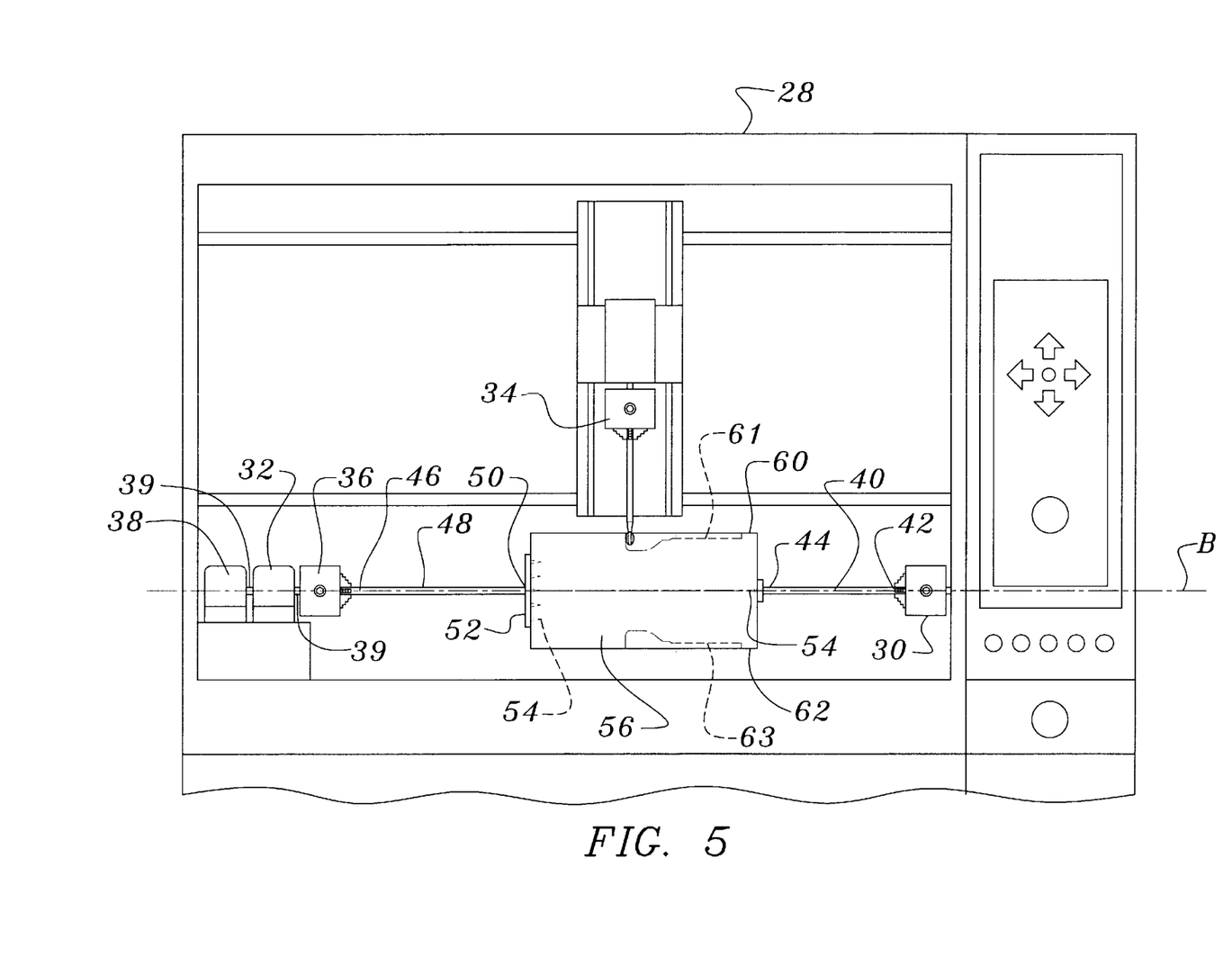
FIG. 5 a front elevational view of a computer controlled milling machine, illustrating cutting the opposed sides of the foam block to form the interior cavity.
Figure 9A:
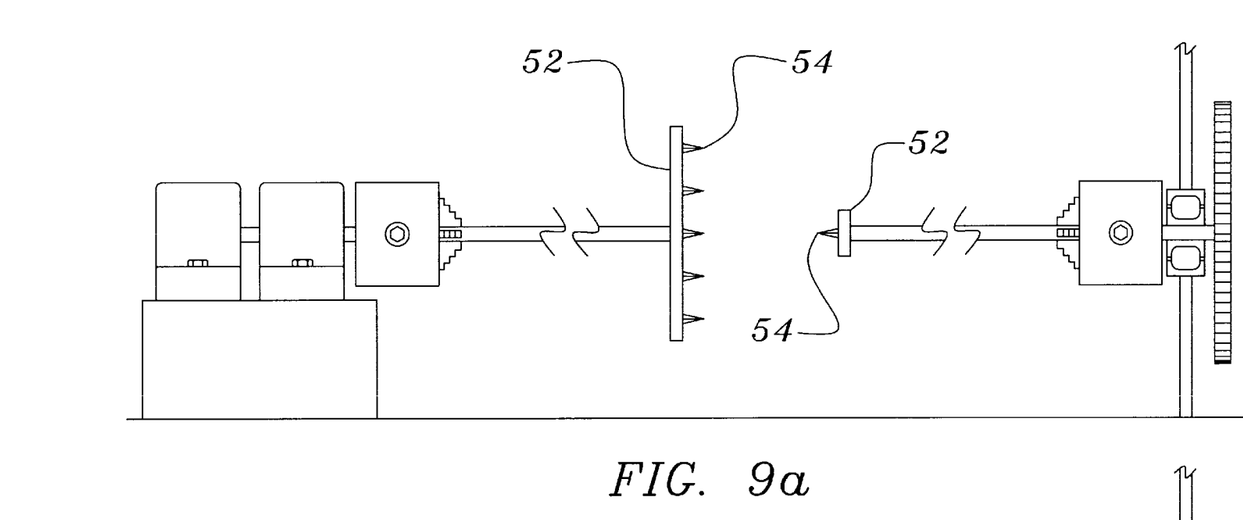
FIG. 9a a detailed view of the milling machine illustrating the apparatus for mounting the foam block in the milling machine.

A computer controlled milling machine 28, for example, model number Pro Series 110-60, large carver, manufactured by Benz Group Ltd., United Kingdom, may be used with certain modifications. The standard Benz carver only has a driven chuck and a through bearing to support the shaft onto which items to be carved are mounted. The shaft has one end mounted in the through bearing for free rotation and free lateral movement and the other end is mounted in the driven chuck for rotation. Mounting a foam blank onto the shaft provides very unsatisfactory results when cutting a foam blank as the cuts will be uneven. It is essential that pressure be applied to both ends of the foam block so that it is slightly compressed. FIG. 5 illustrates the modified milling machine 28, which includes the original driven chuck 30 and the original through bearing 32. A freewheeling chuck 36 and a pillow block bearing 38 are added. The shaft 39 of the freewheeling chuck 36 is mounted in the through bearing 32 for stability and against the pillow block bearing 38 to fix the freewheeling chuck. A first shaft 40 has a first end 42 that is mounted in the driven chuck 30 and it has a second end 44 that extends outwardly therefrom. The first end 46 of a second shaft 48 is mounted in the freewheeling chuck 36 and its second end 50 extends outwardly therefrom so that it is longitudinally opposed to the first shaft. The axes of the driven chuck 30, the first pipe 40, the second pipe 48, the freewheeling chuck 36, the through bearing 32, and the pillow block bearing 38 are all coincident with axis B. As shown in FIG. 9a, on the second ends 44 and 50 of each shaft 40 and 48 respectively are mounted a gripper 52. Each gripper 52 has at least two projections 54 extending outwardly therefrom. These projections 54 are insertable within the foam block, as shown in FIG. 5, gripping the block and preventing its rotation. In a preferred embodiment, as shown in FIG. 9a there are five projections 54 on each gripper 52.

Prior to tightening the shaft 40 in the driven chuck 30 and the shaft 48 in the freewheeling chuck 36, a foam block 56 is mounted between the second ends 44 and 50 of the shafts 40 and 48 respectively so that its longitudinal axis is aligned with axis B. The second ends of the shafts are moved toward one another so that the projections 54 of the grippers 52 engage the foam block 56. Then the second ends of the shafts are moved toward one another to place the block 56 under compression. A medium density soft urethane foam block provides a consistency and feel that is similar to flesh, thereby providing a good cosmetic cover. When using a medium density soft urethane foam block, the ends of the shafts 44 and 50 should be moved between ½ to 1 inch closer to one another to provide the proper amount of compression. The driven and freewheeling chucks are then tightened so that the block 56 remains under compression. These adjustments are not possible without the modification of the Benz carver.

Figure 6:
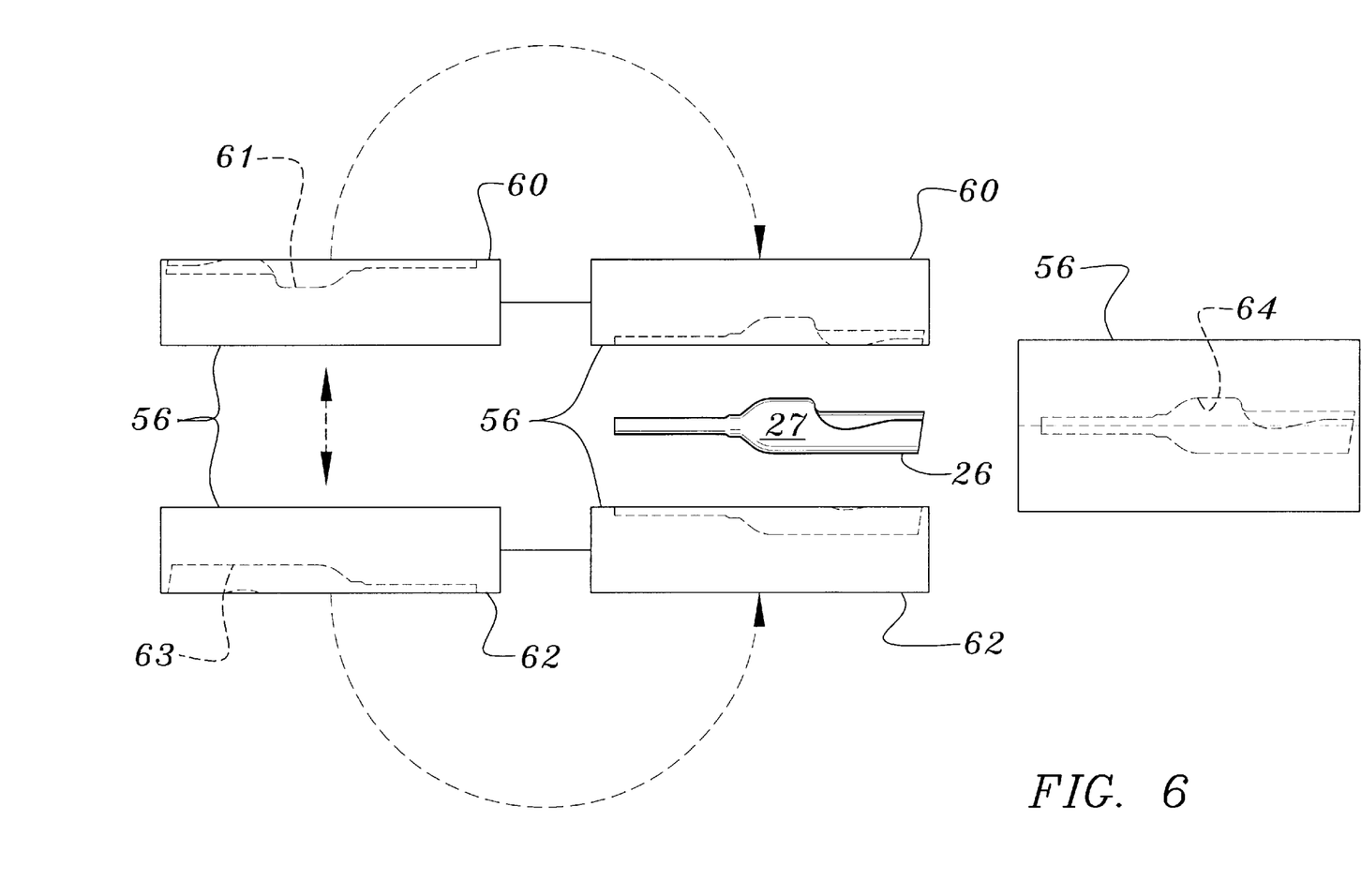
FIG. 6 a view of the cut foam block illustrating the block being flipped longitudinally and the opposing sides of the block being attached together to form the cavity.

With the foam block 56 mounted in the milling machine 28, the computer controlled milling machine 28 is activated, commencing the cutting operation under the control of the installed computer programs and cutting to the dimensions previously downloaded. The driven chuck 30 commences rotation and the cutting head 34 is positioned at the beginning of the cut. As seen in FIG. 5, as the block is rotated, the cutter blade engages the first side 60 of the block 56 moving inwardly and outwardly to carve a portion of one half of the cavity 64, the milling machine's computer program compensating for the rotation of the block. When the opposed second side 62 of the block 56 rotates under the cutting head 34, the cutting head again moves inwardly and then outwardly cutting a portion of the other half of the cavity 64, again compensating for the rotation of the block 60. The cutting head 34 then advances longitudinally to make its second cut on the first side 60 and then on the second side 62, and then continues to advance longitudinally until the entire cavity 64 is cut, forming indentations 61 and 63 on the opposed sides 60 and 62 of the block 56. The foam block 56 is then removed from the milling machine 28 and is cut longitudinally between the indentations 61 and 63 to form two parts of the block as shown in FIG. 6. The foam blocks are then flipped so that the indentations 61 and 63 are facing one another. The two foam blocks are attached together so that the perimeters of the indentations in each block are aligned and coincide with one another, providing a block with a cavity 64 having the general shape of the prosthetic component and formed therein. In a preferred embodiment the blocks 56 are attached to one another by applying glue to both inside surfaces and placing the blocks together and then placing them into a vacuum chamber. Reducing the amount of air in the chamber increases the penetration of the glue into the foam. Once the glue has dried and bonded the blocks together, the block is removed from the vacuum chamber. One end of the block 56 is cut off, so that the largest end of the cavity 64 is exposed. This permits easy access to the prosthetic component for its installation, later adjustment or replacement as necessary.

Figure 7:
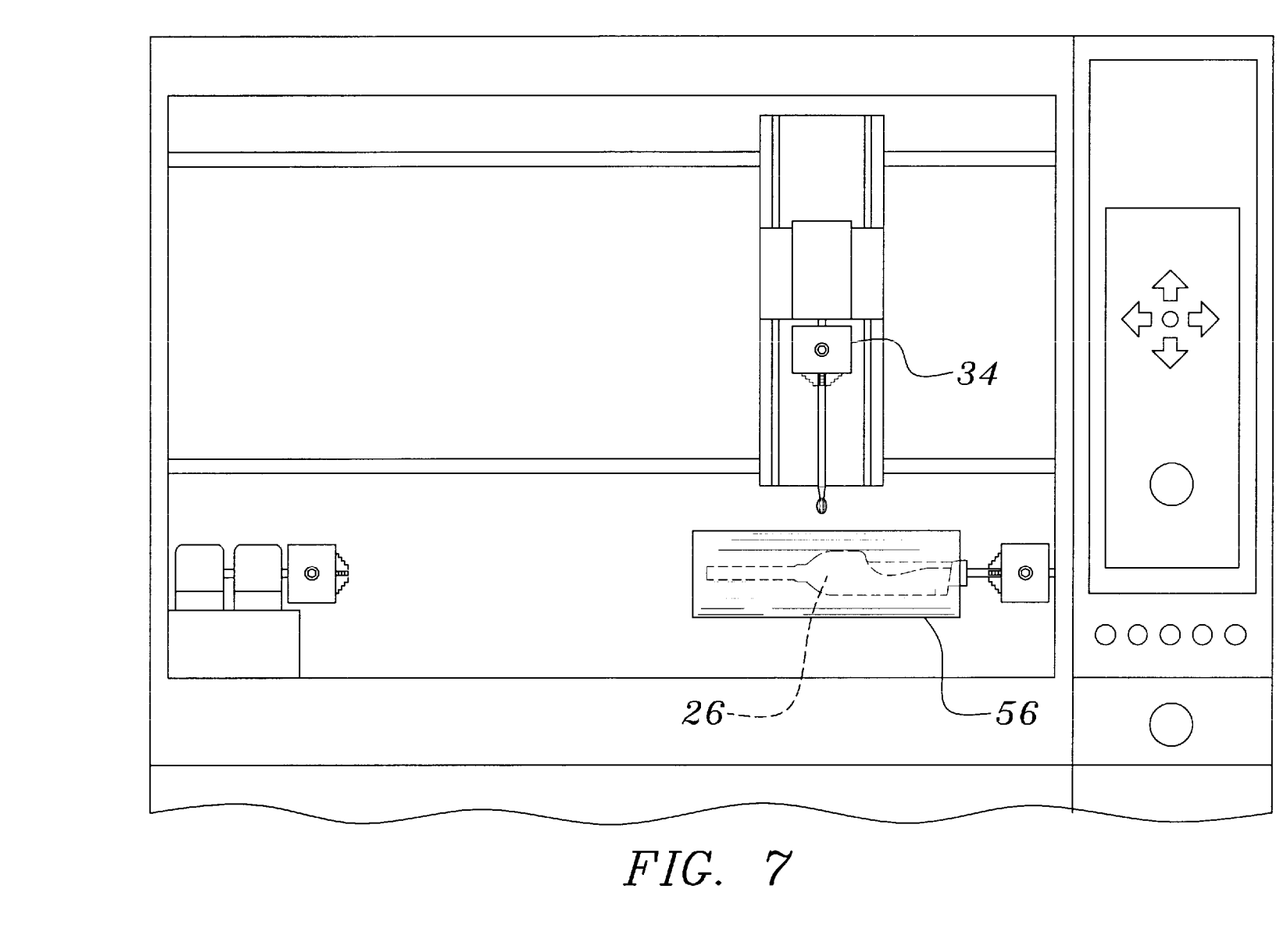
FIG. 7 a view of the milling machine illustrating the block mounted on the replica in preparation for cutting the exterior surface of the block.
Figure 8:
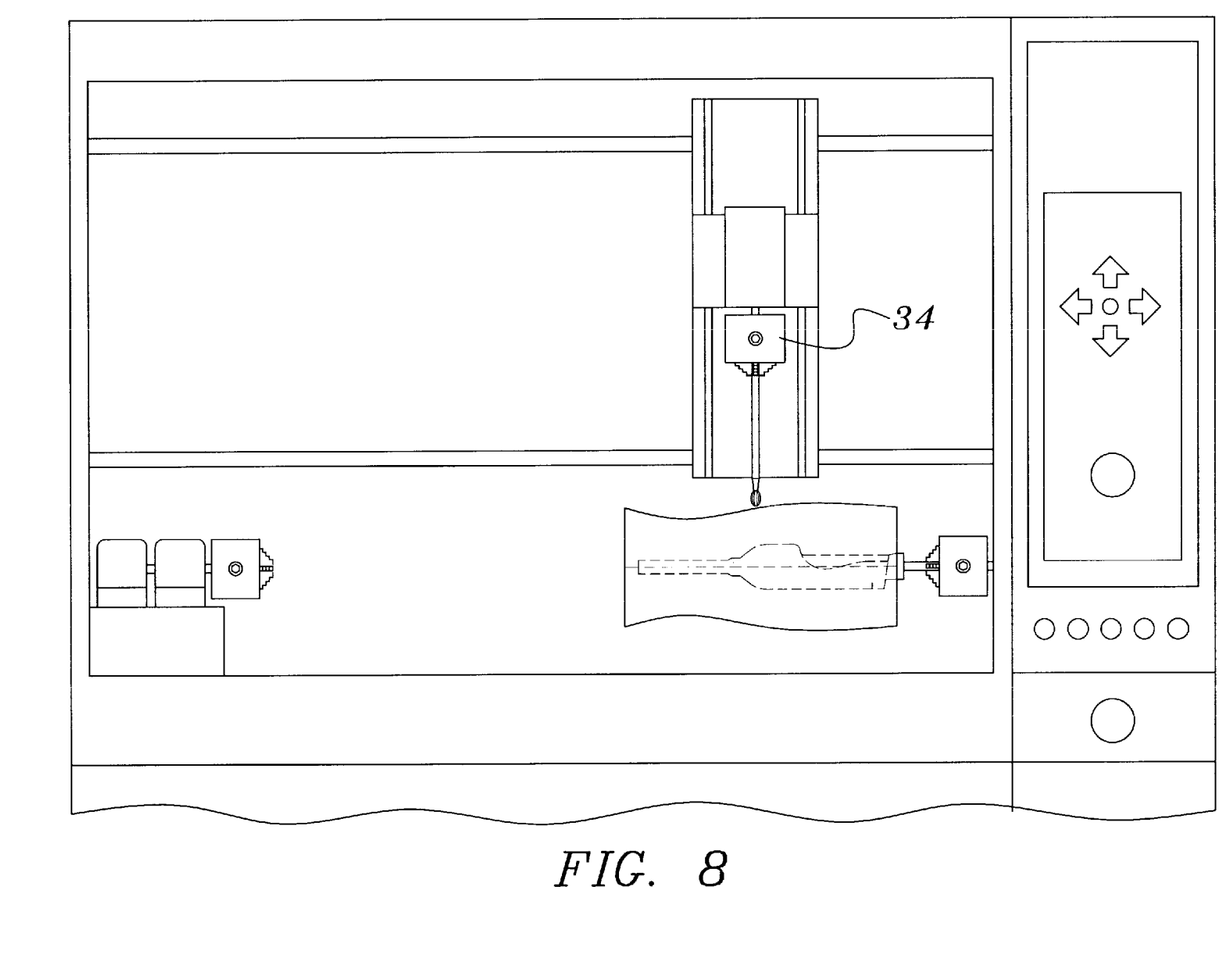
FIG. 8 a view of the milling machine illustrating the block being cut to a predetermined exterior shape to form the cosmetic cover.
Figure 9B:
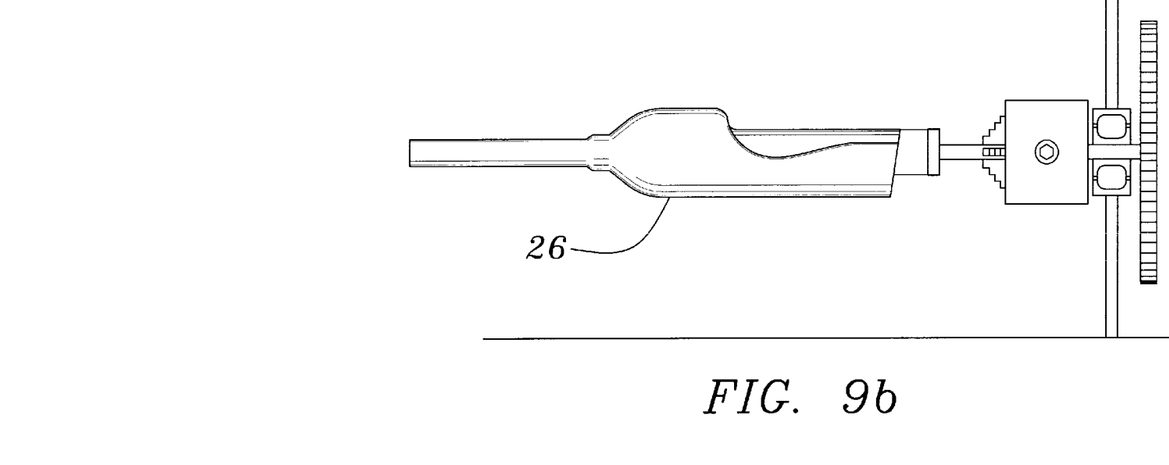
FIG. 9b a detailed view of the milling machine illustrating the apparatus for mounting the replica in the milling machine.

FIGS. 7 and 8 illustrate cutting the exterior surface of the block 56 so that its appearance is as similar to the patient's sound limb as possible. In FIG. 9, the foam replica 26 is mounted in the milling machine as a mandrel to support the foam block 56 while the exterior of the block is being carved. As the foam block 56 rotates the cutting head 34 moves inwardly and outwardly in accordance with the exterior dimensions obtained from a patient. These dimensions may be obtained through the use of the digitizing wand and CAD system, digital photos, a paper tracing, or by a series of manual measurements. In the alternative, the exterior may be left rectangular or it may be carved to a rough standard shape, as shown in FIG. 8, so that the technician installing the prosthesis may complete the final outer shape of the cosmetic cover.

Figure 10:
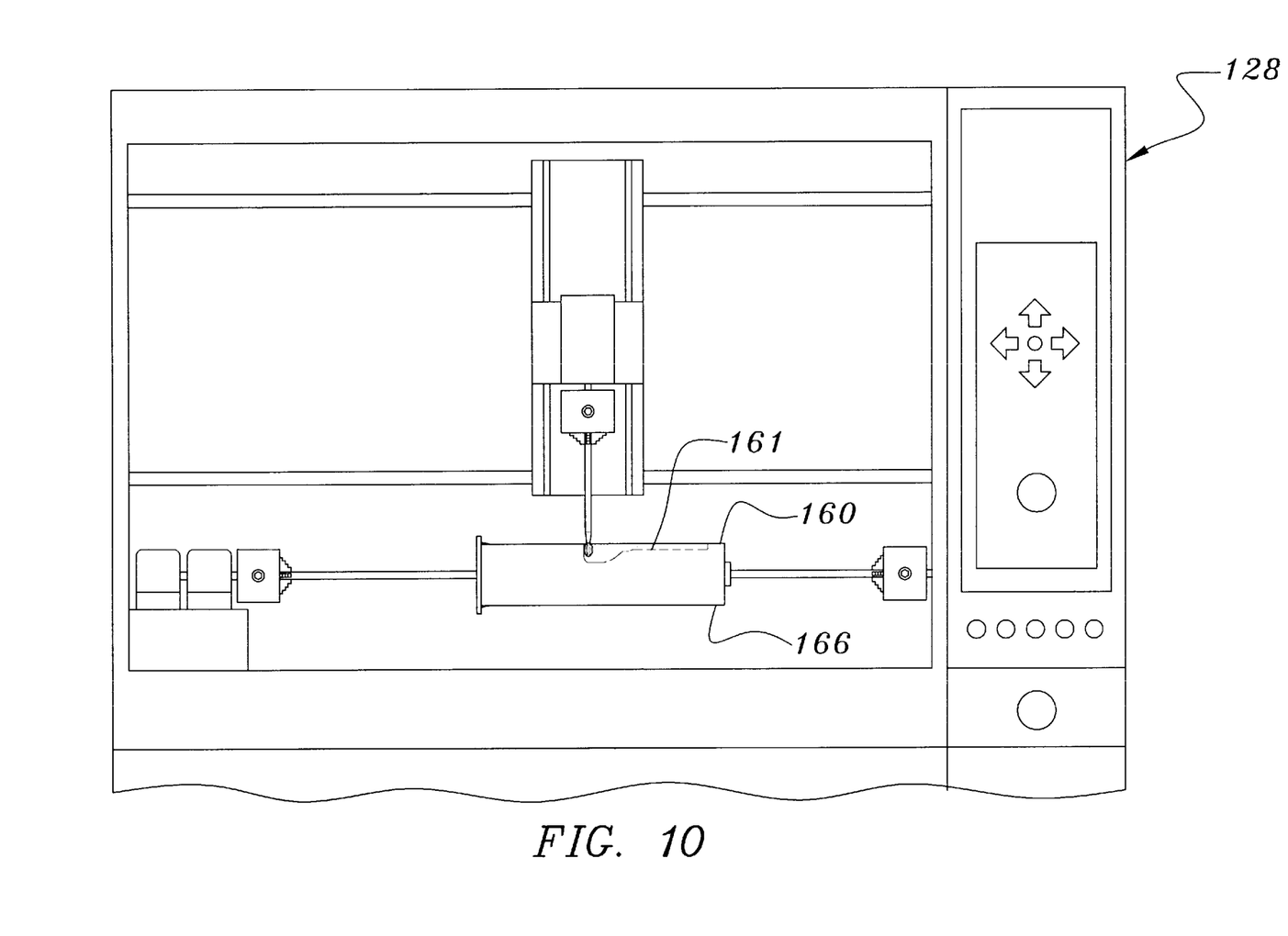
FIG. 10 illustrates another embodiment.

FIG. 10 illustrates an embodiment, in which a block is mounted in the computer controlled milling machine according to the steps previously described. However, the computer of the milling machine 128 is programed to cut the halves of the cavity serially rather than simultaneously. A first block 166 is installed in the milling machine 128 following the same steps of the first embodiment when the foam block 56 was installed, so that the first block 166 will be similarly compressed. The milling machine 128 then cuts one half of the cavity 161 into one side 160 of the first block 166 to form an indentation therein. A second block (not shown) is installed in the same manner as the first block 166, and the other half of the cavity (not shown) is cut into the second block forming an indentation in that block. The two halves are then attached to one another, preferably by gluing according to the steps previously discussed, so that the periphery of the indentations are aligned forming a cavity that is generally the same shape and size as the prosthetic component 10.

In this same embodiment, a single block may be inserted in the milling machine 128 using the same steps described above. The two indentations are then carved in the same side of that block in series. This block is then cut in half between the two indentations and the two parts of the block are joined together with the indentations aligned with one another. The blocks may be joined by gluing or other well-known means suitable for the purpose. By joining the blocks together a cavity is formed therein that has the general shape and size of the prosthetic component 10.

While the foregoing describes particularly preferred embodiments of the present invention, it is to be understood that numerous variations and modifications of the method will occur to those skilled in the art. Accordingly, the foregoing description is to be considered illustrative only of the principles of this invention and is not to be considered limitative thereof, the scope of the invention being determined solely by the claims appended hereto.

What is claimed is:

1. A method for fabricating a cosmetic cover for a prosthetic component comprising the steps of:

selecting a prosthetic component;

collecting data defining the exterior surface of said prosthetic component;

sending said data to a computer-aided design tool, said computer-aided design tool converting said data to define the interior surfaces of two longitudinal halves of a cavity sized and configured to receive said prosthetic component therein;

providing a milling machine that is computer controlled, said milling machine having a first shaft that has a first end and a second end, said first end being mounted to said milling machine, and a longitudinally opposed second shaft having a first end and a second end, said first end being mounted to said milling machine;

downloading said data defining the exterior surface of said two halves of said prosthetic component to said milling machine;

mounting a foam block, having two opposed sides and two opposed ends, in said milling machine so that said opposed ends lie between said second ends of said first and second shafts;

rotating said block;

cutting a portion of one of said two halves of said prosthetic component into one of said opposed sides of said block, and then cutting a portion of the other half of said prosthetic component into the other one of said opposed sides of said block as said block rotates;

longitudinally advancing said cutter until the exterior surface of said prosthetic component is cut into said block forming indentations in the opposed sides of said block that correspond to the exterior surface of said prosthetic component;

removing said block from said milling machine and cutting said block longitudinally between said indentations to form two parts of said block;

attaching the two parts of said block together such that the perimeters of the indentations coincide and a cavity having the general shape of said exterior surface of said prosthetic component is formed therein.

2. A method for fabricating a cosmetic cover for a prosthetic component as in claim 1 wherein said step of collecting said data defining the exterior surface further comprises the steps of:

creating a mold of the prosthetic component;

constructing a replica of the prosthetic component from said mold; and collecting said data generally defining the exterior surface of said prosthetic component from said replica.

3. A method for fabricating a cosmetic cover for a prosthetic component as in claim 1 wherein the step of mounting said block in said milling machine comprises the further steps of:

moving said second end of at least one of said first and second shafts toward the second end of the other one of said shafts such that said block is compressed; and holding said block in said compressed state until said cutting step is completed.

4. A method for fabricating a cosmetic cover for a prosthetic component as in claim 1 further comprising the step of mounting a gripper on said second ends of said first and second shafts, each gripper having at least two projections extending inwardly into said opposing ends of said block.

5. A method for fabricating a cosmetic cover for a prosthetic component as in claim 1 further comprising the step of rotating said first chuck and permitting said second chuck to freely rotate.

6. A method for fabricating a cosmetic cover for a prosthetic component as in claim 1, comprising the additional steps of:

inserting said replica of said prosthetic component into said cavity in said block;

mounting said replica in said milling machine;

determining the outer surface dimensions of said cosmetic cover;

downloading said outer surface dimensions of said cosmetic cover into said milling machine; and cutting said exterior of said block to said outer surface dimensions.

* * * * *